United States Patent
Klein et al.

(10) Patent No.: US 6,250,152 B1
(45) Date of Patent: *Jun. 26, 2001

(54) SENSOR ARRANGEMENT

(75) Inventors: Manfred Klein, Geislingen; Anton Knoll, Ulm; Klaus Land, Denkendorf; Rudolf Thom, Stuttgart; Harald Ott, Kleinsachsenheim, all of (DE)

(73) Assignee: DaimlerChrysler AG, Stuttgart (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/914,000
(22) PCT Filed: Mar. 6, 1996
(86) PCT No.: PCT/EP96/00928
  § 371 Date: Dec. 29, 1997
  § 102(e) Date: Dec. 29, 1997
(87) PCT Pub. No.: WO96/30758
  PCT Pub. Date: Oct. 3, 1996

(30) Foreign Application Priority Data

Mar. 29, 1995 (DE) ................ 195 11 556

(51) Int. Cl.$^7$ ............. G01F 23/26; G01R 27/26
(52) U.S. Cl. ............. 73/304 C; 324/690; 361/284
(58) Field of Search ............. 73/304 C, 290 R, 73/304 R; 324/690; 361/284

(56) References Cited

U.S. PATENT DOCUMENTS

| | | | |
|---|---|---|---|
| 2,710,541 | * 6/1955 | Miller | 73/304 C |
| 2,848,666 | * 8/1958 | Zito | 361/284 |
| 2,864,981 | * 12/1958 | De Giers | 73/304 C X |
| 4,451,894 | * 5/1984 | Doughherty et al. | 364/509 |
| 4,590,575 | 5/1986 | Emplit | 364/509 |
| 4,629,334 | 12/1986 | Hochstein | 374/103 |
| 4,646,070 | 2/1987 | Yasuhara et al. | 340/603 |
| 4,745,893 | 5/1988 | Atherton et al. . | |
| 4,924,702 | 5/1990 | Park . | |
| 5,187,979 | * 2/1993 | Edmark, III | 73/304 C |
| 5,406,843 | * 4/1995 | Hannan et al. | 73/304 C |
| 5,477,727 | * 12/1995 | Koga | 73/304 C |

FOREIGN PATENT DOCUMENTS

| | | |
|---|---|---|
| 2949386 | 6/1980 | (DE) . |
| 2908449 | 9/1980 | (DE) . |
| 3041914 | 6/1982 | (DE) . |
| 0378304 | 7/1990 | (EP) . |
| 110919 | * 8/1980 | (JP) ..... 73/304 C |
| 1538055 | * 1/1990 | (SU) ..... 73/304 C |

* cited by examiner

*Primary Examiner*—Hezron Williams
*Assistant Examiner*—Michael Cygan
(74) *Attorney, Agent, or Firm*—Venable; George H. Spencer; Norman N. Kunitz

(57) ABSTRACT

A sensor arrangement determines a condition and level of a liquid in a container. A first sensor has first electrodes forming a first measuring chamber communicating with the liquid and supplies a signal for determining an impedance of the first sensor and a condition of the liquid in the container. A second sensor has second electrodes forming a second measuring chamber communicating with the liquid via the first measuring chamber and supplies a signal for determining an impedance of the second sensor and a level of the liquid in the container. Electronic devices are coupled to the first and second sensors, and determine the impedance of the first and second sensors and the condition and level of the liquid in the container.

22 Claims, 2 Drawing Sheets

SENSOR ARRANGEMENT

FIELD OF THE INVENTION

The invention relates to a sensor arrangement for determining the condition and level of a liquid in a container.

BACKGROUND OF THE INVENTION

U.S. Pat. No. 4,646,070 discloses an arrangement for determining the aging condition of lubricating oil in internal combustion engines, the dielectric constant of the oil is determined by means of a capacitive sensor, whose electrode measuring chamber is filled entirely with the lubricating oil, and a statement regarding the aging condition of the oil is derived therefrom.

U.S. Pat. No. 4,629,334 discloses a sensor arrangement wherein, by measuring the resistance of an oil disposed between the electrodes of an electric sensor, the aging condition of the oil is inferred. By way of simultaneous measurement of the temperature with an integrated temperature sensor, it is possible to compensate for temperature dependencies of the oil resistance. The electrical evaluation device additionally provides a detector which triggers an alarm signal if conductive oil between the electrodes of the sensor is missing.

Electrical sensors are also used for the level measurement of liquids in containers, for example, U.S. Pat. No. 4,745,893 teaches that the capacitance of a partially liquid-filled capacitor can be evaluated as a level measure.

Further examples of level sensors are disclosed in U.S. Pat. No. 4,924,702 and EP-A 0 378 304. U.S. Pat. No. 4,924,702 describes a level sensor having a measuring capacitor and a reference capacitor. The ratio of the measured values of the measuring capacitor and the reference capacitor is used for determining the level of a liquid in the measuring capacitor. The reference capacitor serves to obtain a level measurement independently of the conductance and the dielectric constant. Further, EP-A 0 378 304 proposes a sensor for the level measurement having a measuring capacitance and a reference capacitance. The level signal is composed of the measuring capacitance and the reference capacitance and thus permits a more precise level determination.

SUMMARY OF THE INVENTION

It is the object of the present invention to propose an advantageous sensor arrangement for determining the condition and level of a liquid in a container.

The invention includes a sensor arrangement for determining the condition of a liquid in a container. The arrangement has a first sensor with electrodes forming a first measuring chamber filled with the liquid and has electrical devices for the measurement of the impedance of the first sensor and for the derivation of a condition signal. The arrangement further has a second sensor with electrodes forming a second measuring chamber and is provided as a level sensor having a measuring chamber partially filled with the liquid as a function of the level in the container. The electrical devices derive a level signal from the measurement of the impedance of the second sensor. The measured impedance of the first sensor is used for the calibration of the impedance measurement of the second sensor. The measuring chamber of the second sensor is in communication with the liquid in the container via the measuring chamber of the first sensor by way of an opening arranged at the foot of the first sensor.

Additionally, the sensor arrangement can include an auxiliary chamber that is in communication with the liquid in the container via the measuring chamber of the first sensor and is disposed above the measuring chamber of the first sensor. Further, the horizontal cross section of the auxiliary chamber is larger than that of the measuring chamber of the second sensor.

In addition, for the sensor arrangement, the first and second sensors are each comprised of coaxial cylindrical electrodes. The first and second sensors include a joint outer cylinder electrode and separate internal cylinder electrodes arranged axially inside the joint outer cylinder electrode. The internal cylinder electrodes with insulating elements are embodied as a structural unit that can be plugged into the outer electrode. Further, the sensor arrangement can be used as a lubricating oil sensor in an engine.

The invention provides an arrangement which can be executed in a compact manner and which, in a simple manner, permits a reliable measurement of quality and level of a liquid in a container. The arrangement can be implemented to be mechanically and electrically straightforward and robust and is therefore particularly suited for use in vehicle engines.

BRIEF DESCRIPTION OF THE DRAWINGS

The invention is illustrated in detail in the following by way of embodiments with reference to the figures.

DESCRIPTION OF THE INVENTION

Figure 1:
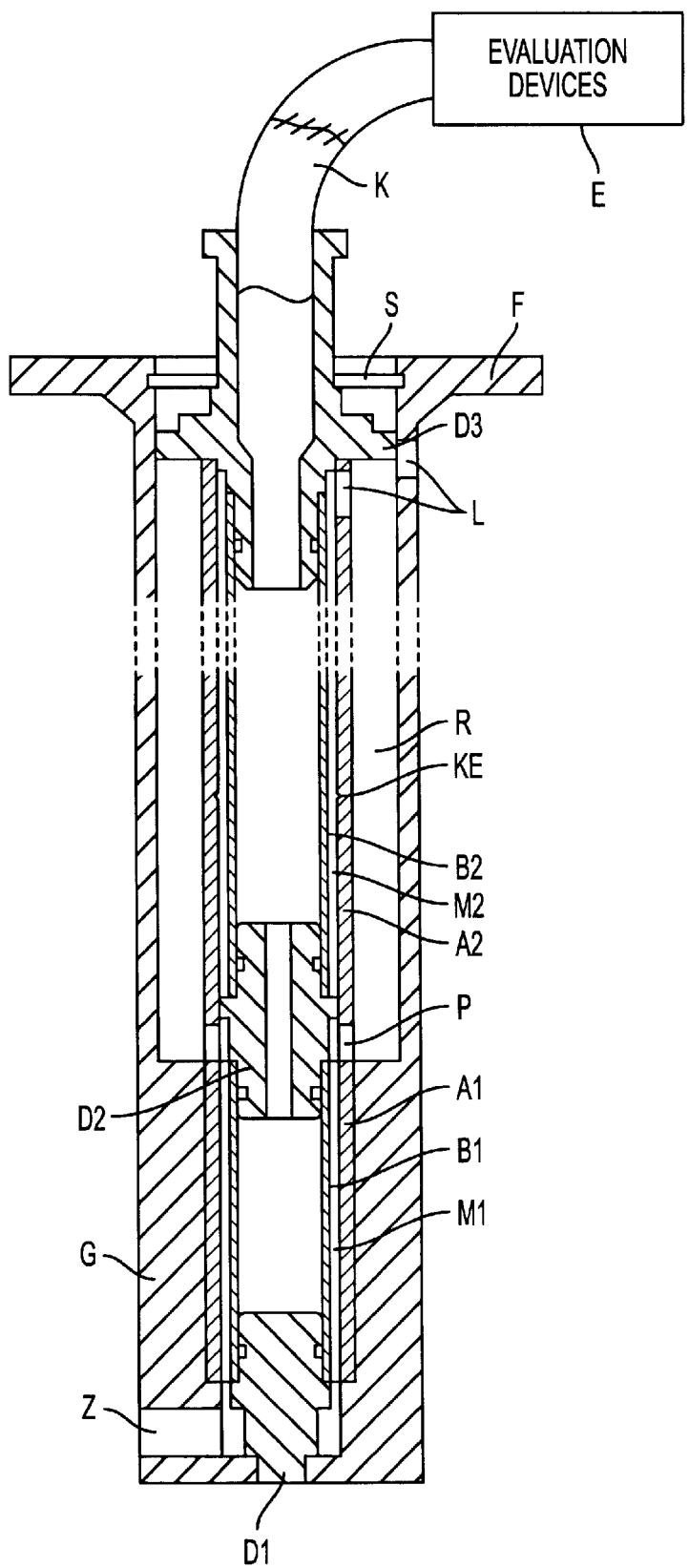
FIG. 1 depicts a preferred embodiment of a sensor arrangement.

In the arrangement shown in FIG. 1, a housing G accommodates a first sensor having an outer electrode A1 and an internal electrode B1 and a second sensor having an outer electrode A2 and an internal electrode B2. The electrodes are circular cylindrical tubes which are coaxially arranged and form between them a first measuring chamber M1 of the first sensor and a second measuring chamber M2 of the second sensor. The tubes may be metallic or they may also be comprised of surface-metallized plastic.

The outer electrodes A1 and A2 are preferably electrically connected and form a uniform continuous tube which is fixedly embedded in the housing G. The internal electrodes B1 and B2 are insulated with respect to one another and with respect to the outer electrodes by means of spacer elements D1, D2, and D3, which are made from a non-conductive material, preferably plastic, and geometrically fixed. Preferably, the spacer elements D1, D2, and D3 form a fixedly joined and encapsulated structural unit with the internal electrodes B1 and B2. The unit can be plugged into the housing and the outer electrodes in a self-adjusting manner and held, for example, by a securing disk or a securing ring S.

In the indicated example, the lower spacer element D1 engages a recess at the foot of the housing G in a centering manner. The middle spacer element D2 centers the internal electrodes within the outer electrodes by means of several spacer embossments distributed over its circumferences. The upper spacer element D3 centers and fixes the internal and outer electrodes with respect to one another and in the housing and closes off the inside of the housing towards the top. A securing flange F is provided on the upper housing edge. For the electrical connection to evaluation devices E, a cable K is inserted into an opening of the upper spacer element D3 and is encapsulated and fixed, for example, through gluing or plugging. The middle spacer element D2 has a leadthrough for the electrical feed to the internal electrode B1 of the first sensor. The electrical contacting can take place, for example, via spring contacts inserted so as to be clamping.

An additional or auxiliary chamber R can be provided between the outer electrode A2 of the second sensor and the housing wall, as illustrated. The inside of the housing is in communication with the liquid in the container via one or several openings Z at the lower housing edge in the manner of communicating tubes. The sensor housing can also be arranged so as to be spatially removed from the container if the liquid level in the container communicates with the liquid level in the sensor housing by way of a tube, hose, conduit, or similar connection. The openings Z can be provided with a protective sieve against particle impurities. The function of a particle sieve can also be realized by way of the structural design of the housing and/or of the spacer elements in such a manner that the effective flow-through cross sections are formed by a plurality of openings having a small cross section. Ventilation openings L at the upper edge of the measuring chamber M2 and of the additional chamber R ensure that inflow and discharge of liquid take place without pressure differences.

During this process, the measuring chamber M2 of the second sensor and the optionally available additional chamber R are preferably in communication with the container liquid only above the measuring chamber M1 of the first sensor so that, with changing liquid levels, a regular inflow of new container liquid into the measuring chamber M1 of the first sensor is ensured. For this purpose, holes P are provided for both outer electrodes A1 and A2 above the first sensor, the tube being continuous. The additional chamber R, whose horizontal cross sectional surface is preferably dimensioned to be larger than that of measuring chamber M1, causes a liquid throughput through the measuring chamber M1 which, as a rule, exceeds the volume of measuring chamber M1, even at rather small level fluctuations of the container liquid, and thus results in a regular exchange of the liquid in measuring chamber M1. In contrast, the cross section of measuring chamber M2 can be limited by the measurement method, particularly for capacitive measurements.

The dimensioning of the volume of the measuring chamber M2 and of the additional chamber R, on the one hand, and the flow cross sections of the first measuring chamber M1 and openings Z, on the other hand can be matched advantageously such that short-term level fluctuations are damped. Instead or in addition, the compensation of level fluctuations can also take place electronically during the evaluation.

In the following, the sensor arrangement is preferably used as a lubricating oil sensor in an internal combustion engine.

Preferably, the arrangement is dimensioned such that, during regular operation, the lower first measuring chamber M1 of the first sensor is completely filled with oil, and the upper second measuring chamber M2 of the second sensor is partially filled with oil.

Therefore, the measurement of the impedance of the first sensor supplies a level-independent measuring value from which a condition signal can be derived as an assessment of the degree of aging or of the quality of the oil by way of comparison with reference values which are stored or are set as threshold values. The reference values are obtained, for example, through measurement with new oils.

The impedance of the second sensor is primarily dependent on the actual level and to a small extent, on the condition of the oil. The impedance value measured with the first sensor is used for the calibration of the measured impedance value of the second sensor. Thereby the influence of the aging-dependent changes of the electrical or dielectrical properties of the oil can be compensated during the level measurement.

By way of a temperature probe, which can be integrated easily, preferably on the inside of the electrode B1, the sensor arrangement can be supplemented for measuring the temperature as a further operating parameter. Therewith, temperature influences in the impedance values can optionally also be compensated.

For engines having a small structural height, the use of the first sensor only for the level-independent quality determination of the oil may require a reduction in the height of the first sensor, resulting in very small impedance values which, as a consequence, are more difficult to pick up metrologically. In such cases, the entire level range to be detected is not covered by the upper second sensor, and the lower first sensor is used to determine the oil quality when measuring chamber M1 is filled completely and to detect low levels when measuring chamber M1 is only partially filled.

Measured impedance values of the lower first sensor are only evaluated for the quality determination and as a calibration reference when the measuring chamber M1 of the first sensor is entirely filled with oil. This can be assumed to be the case, for example, if the presence of at least a small amount of oil in measuring chamber M2 of the second sensor can be determined from the impedance value of the second sensor. The impedance value of the first sensor measured in such a case is stored as a condition signal for the quality of the oil and as calibration reference. The stored value is updated by new impedance values of the first sensor valid for a completely filled first measuring chamber M1. By way of the stored impedance value, a level can be determined from the impedance value of an only partially filled first measuring chamber. Advantageously, the parting line between the first and second sensors can be moved to a height which corresponds to the oil level in the oil pan for a minimum oil fill amount and a higher rotational speed of the engine. In the normal operating condition, the lower first sensor then supplies a quality signal, and the upper second sensor supplies a level signal, as has been described above in detail. If the oil level drops below the height of the parting line due to a decreasing oil fill amount and/or extreme operating conditions, a low-level signal can be obtained from the measured impedance of the first signal. This condition can also serve as a criterion for an oil refill display or as a trigger for an oil loss alarm signal.

In order to accomplish a high measurement precision for, capacitive measurements, it is advantageous if both sensors have identical capacitance values, and the measurement range of a downstream electronic unit is thus utilized to an optimum extent. This is particularly important if both sensors are connected with a joint electronic evaluation unit via a multiplex circuit so as to alternate in time.

This can be accomplished through comparable structural heights for identical transverse dimensions or through different transverse dimensions for markedly varying structural heights.

The calibration of the impedance value of the second sensor, by way of the level-independent impedance value of the first sensor, can be supported or possibly replaced by a self-calibration of the second sensor using a discontinuity in the level/impedance characteristic, which is included therein in a targeted manner. For this purpose, for example, a cut, a notch, or the like KE can be made in one of the electrodes of the sensor which, for a continuous level change, effect a jump in the signal sequence over time which can be detected, for example, by a differentiating stage. The then current impedance value can be associated with a specific level according to the position of the cut etc., thus resulting in the calibration option. A design with several marks is possible, with the marks being correlated, for example, with a level maximum or level minimum.

Figures 2A, 2B:
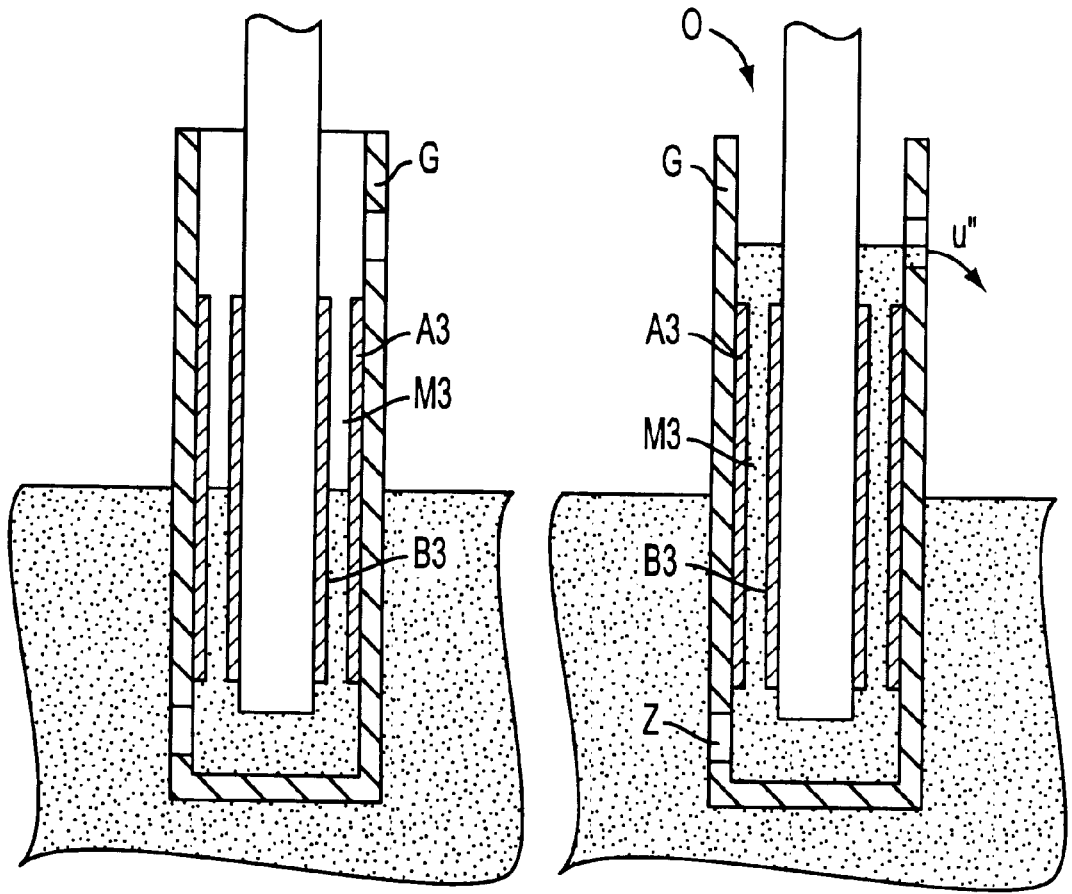
FIG. 2 depicts an alternative embodiment.

An alternative embodiment for the arrangement illustrated in FIG. 1 of two sensors on top of one another is represented schematically in FIG. 2. Here, the two sensors are realized by one and the same electrode arrangement which, in time multiplex, serve as a first sensor for the level-independent quality measurement and as a second sensor for the level measurement. For this purpose, a measuring chamber M3 has electrodes A3 and B3, which, for example, can again be designed as circular cylinders placed inside of one another. The measuring chamber M3 is connected for the level measurement in the manner of communicating tubes to the oil container via an opening Z arranged at the foot of the sensor and supplies a level-dependent signal during the impedance measurement (FIG. 2a). For the level-independent impedance measurement (FIG. 2b), the oil level in measuring chamber M3 is replenished from on top, for example, via a pump, up to an overflow Ü, which is above the maximum level gauge of the container, by means of a targeted additional supply O of oil, and then the sensor impedance is measured. The through-flow-limiting dimensioning of the lower measuring chamber opening ensures easy refilling of the measuring chamber. For the renewed level measurement, the additional oil supply is shut off, and oil is discharged through the opening at the foot of the sensor arrangement, and the container level appears in the measuring chamber. The additional oil supply can be added and switched off, for example, through a valve or a flap whose operation takes place, for example, in a temperature-controlled manner via bimetal elements or memory metal elements. From the discharge behavior of the oil during the transition from the quality measurement to the level measurement or the associated time sequence of the sensor impedance, further statements can be derived regarding the quality condition of the oil, if necessary. The level-independent measurement can again serve to determine the quality and to calibrate the level measurement.

Different methods are known per se for measuring the impedance, particularly conductivity and capacitance determinations.

The electrodes can have any form per se. Conceivable electrodes are, in particular, interdigital structures on insulating substrates. In addition to the sensors that were described, the arrangement can also comprise a separate limit value sensor which merely detects the presence of oil at a particularly low level.

What is claimed is:

1. A sensor arrangement for determining a condition of a liquid in a container and a level of the liquid in the container comprising:
   a first sensor having first electrodes forming a first measuring chamber communicating with the liquid in the container via an opening at a lower end of the first sensor, the first sensor supplying a first signal for use in determining an impedance of the first sensor and the condition of the liquid in the container when the first measuring chamber is filled with the liquid;
   a second sensor having second electrodes forming a second measuring chamber coupled to the first measuring chamber and communicating with the liquid in the container only via the first measuring chamber, the second sensor supplying a second signal for use in determining an impedance of the second sensor and the level of the liquid in the container when the second measuring chamber is partially filled with the liquid;
   a common housing in which the first and second sensors are disposed, with a lower end of the second sensor being disposed above an upper end of the first sensor, and with the second measuring chamber being coupled to the first measuring chamber and in communication with the liquid in the container via at least one opening that is disposed completely within the housing connecting the lower end of the second measuring chamber to the upper end of the first measuring chamber; whereby,
   means, coupled to the first and second sensors, receives the first and second signals, and determines the impedance of the first sensor from the first signal and the condition of the liquid in the container therefrom, determines the impedance of the second sensor from the second signal and the level of the liquid in the container therefrom, and calibrates the impedance of the second sensor.

2. A sensor arrangement according to claim 1, further comprising a further separate auxiliary chamber communicating with the liquid in the container only via the measuring chamber of the first sensor and disposed above higher end of the first sensor.

3. A sensor arrangement according to claim 2, wherein the auxiliary chamber has a horizontal cross section larger than a horizontal cross section of the measuring chamber of the second sensor.

4. A sensor arrangement according to claim 1, wherein the electrodes of the first and second sensors each comprise coaxial cylindrical electrodes.

5. A sensor arrangement according to claim 4, wherein the coaxial cylindrical electrodes of the first and second sensors comprise a joint outer cylindrical electrode and separate first and second internal cylinder electrodes arranged axially inside the joint outer cylindrical electrode.

6. A sensor arrangement according to claim 5, wherein the internal cylindrical electrodes have insulating elements forming a structural unit, the structural unit being plugged into the joint outer cylindrical electrode.

7. A sensor arrangement according to claim 1, wherein the liquid is a lubricating oil in an engine.

8. A sensor arrangement according to claim 1, wherein the means calibrates the impedance of the second sensor using the impedance of the first sensor.

9. A sensor arrangement according to claim 1, wherein an electrode of the second sensor has a discontinuity, and the means calibrates the impedance of the second sensor using the second signal from the second sensor.

10. A sensor arrangement according to claim 2 wherein said electrodes of the first and second sensors each comprise coaxial cylindrical electrodes; and, said auxiliary chamber is disposed within said housing between an outer one of the cylindrical electrodes of the second sensor and an outer wall of said housing.

11. A sensor arrangement according to claim 10 wherein at least one opening to the atmosphere is provided in an upper end of each of the auxiliary chamber and of the second measuring chamber.

12. A sensor arrangement for determining a condition of a liquid in a container and a level of the liquid in the container comprising:

a first sensor having first electrodes forming a first measuring chamber communicating with the liquid in the container via an opening at a lower end of the first sensor, the first sensor supplying a first signal for use in determining an impedance of the first sensor and the condition of the liquid in the container when the first measuring chamber is filled with the liquid;

a second sensor having second electrodes forming a second measuring chamber coupled to the first measuring chamber and communicating with the liquid in the container via the first measuring chamber, the second sensor supplying a second signal for use in determining an impedance of the second sensor and the level of the liquid in the container when the second measuring chamber is partially filled with the liquid;

a further separate auxiliary chamber communicating with the liquid in the container only via the measuring chamber of the first sensor and disposed above a higher end of the first sensor;

a common housing in which the first and second sensors and the auxiliary chamber are disposed, with the electrodes of the first and second sensors each comprising coaxial cylindrical electrodes, with the second sensor being disposed above said higher end of the first sensor, and with said auxiliary chamber being disposed within said housing between an outer one of the cylindrical electrodes of the second sensor and an outer wall of said housing; and, means, coupled to the first and second sensors, receives the first and second signals, and determines the impedance of the first sensor from the first signal and the condition of the liquid in the container therefrom, determines the impedance of the second sensor from the second signal and the level of the liquid in the container therefrom, and calibrates the impedance of the second sensor.

13. A sensor arrangement for determining a condition of a liquid in a container and a level of the liquid in the container comprising:

a first sensor having first electrodes forming a first measuring chamber communicating with the liquid in the container via an opening at a lower end of the first sensor, the first sensor supplying a first signal for use in determining an impedance of the first sensor and the condition of the liquid in the container when the first measuring chamber is filled with the liquid;

a second sensor having second electrodes forming a second measuring chamber coupled to the first measuring chamber and communicating with the liquid in the container only via the first measuring chamber, the second sensor supplying a second signal for use in determining an impedance of the second sensor and the level of the liquid in the container when the second measuring chamber is partially filled with the liquid; and, a common housing in which the first and second sensors are disposed, with a lower end of the second sensor being disposed above an upper end of the first sensor, and with the second measuring chamber being coupled to the first measuring chamber and in communication with the liquid in the container via at least one opening that is disposed completely within the housing connecting the lower end of the second measuring chamber to the upper end of the first measuring chamber.

14. A sensor arrangement according to claim 13, wherein the electrodes of the first and second sensors each comprise coaxial cylindrical electrodes.

15. A sensor arrangement according to claim 14 wherein the coaxial cylindrical electrodes of the first and second sensors comprise a joint cylindrical electrode and separate first and second electrodes arranged axially inside the joint outer cylindrical electrode.

16. A sensor arrangement according to claim 15 wherein the internal cylindrical electrodes have insulating elements forming a structural unit, with the structural unit being plugged into the joint cylindrical electrode.

17. A sensor arrangement according to claim 13 wherein the liquid is a lubricating oil in an engine.

18. A sensor arrangement according to claim 13, wherein an electrode of the second sensor has a discontinuity.

19. A sensor arrangement according to claim 13, further comprising a further separate auxiliary chamber communicating with the liquid in the container only via the measuring chamber of the first sensor and disposed above a higher end of the first sensor.

20. A sensor arrangement according to claim 19 wherein the auxiliary chamber has a horizontal cross section larger than a horizontal cross section of the measuring chamber of the second sensor.

21. A sensor arrangement according to claim 19, wherein said electrodes of the first and second sensors each comprise coaxial cylindrical electrodes; and, said auxiliary chamber is disposed within said housing between an outer one of the cylindrical electrodes of the second sensor and an outer wall of said housing.

22. A sensor arrangement according to claim 21 wherein at least one opening to the atmosphere is provided in an upper end of each of the auxiliary chamber and of the second measuring chamber.

* * * * *